United States Patent
Alaimo et al.

(10) Patent No.: US 7,008,386 B2
(45) Date of Patent: Mar. 7, 2006

(54) FOOT ORTHOTIC

(75) Inventors: Jeffrey M. Alaimo, Lutz, FL (US); Gregory A. Alaimo, Tampa, FL (US)

(73) Assignee: ACOR Orthopaedic, Inc., Cleveland, OH (US)

( * ) Notice: Subject to any disclaimer, the term of this patent is extended or adjusted under 35 U.S.C. 154(b) by 0 days.

(21) Appl. No.: 10/648,065

(22) Filed: Aug. 26, 2003

(65) Prior Publication Data

US 2005/0047677 A1   Mar. 3, 2005

(51) Int. Cl.
  A61B 5/117 (2006.01)
  G01B 11/24 (2006.01)
  G02B 11/30 (2006.01)
  G06K 9/36 (2006.01)
  G06K 9/62 (2006.01)

(52) U.S. Cl. .................... 600/592; 12/142 N; 382/154; 382/286; 356/607

(58) Field of Classification Search .................. 12/1 R, 12/1 G, 142 N, 146 M, 142 R; 700/98, 233; 382/154, 286; 356/601, 607; 600/592
See application file for complete search history.

(56) References Cited

U.S. PATENT DOCUMENTS

| | | | | |
|---|---|---|---|---|
| 2,999,256 A | * | 9/1961 | Mott ........................ 12/142 N |
| 4,510,636 A | * | 4/1985 | Phillips ........................ 12/1 R |
| 4,520,581 A | | 6/1985 | Irwin | |
| 4,826,497 A | | 5/1989 | Marcus | |
| 4,868,945 A | | 9/1989 | DeBettignies | |
| 4,876,758 A | * | 10/1989 | Rolloff et al. ............ 12/142 N |
| 5,083,910 A | | 1/1992 | Abshire | |
| 5,163,094 A | | 11/1992 | Prokoski | |
| 5,164,793 A | * | 11/1992 | Wolfersberger et al. ..... 356/607 |
| 5,339,252 A | * | 8/1994 | White et al. ................. 700/98 |
| 5,432,000 A | | 7/1995 | Young | |
| 5,498,478 A | | 3/1996 | Hansen | |
| 5,678,566 A | * | 10/1997 | Dribbon ..................... 600/592 |
| 5,714,098 A | * | 2/1998 | Potter ........................ 12/142 R |
| 5,733,647 A | | 3/1998 | Moore | |
| 5,800,364 A | * | 9/1998 | Glennie et al. ............. 600/592 |
| 5,879,725 A | | 3/1999 | Potter | |
| 5,951,799 A | | 9/1999 | Williamson | |
| 6,006,412 A | * | 12/1999 | Bergmann et al. ....... 29/407.04 |
| 6,042,759 A | * | 3/2000 | Marshall .................... 264/40.1 |
| 6,141,889 A | | 11/2000 | Baum | |
| 6,160,264 A | * | 12/2000 | Rebiere ................. 250/559.22 |
| 6,170,177 B1 | * | 1/2001 | Frappier et al. .......... 12/142 R |
| 6,247,250 B1 | | 6/2001 | Hauser | |
| 6,280,815 B1 | | 8/2001 | Ersfeld | |
| 6,331,893 B1 | * | 12/2001 | Brown et al. ............... 356/601 |
| 6,481,120 B1 | | 11/2002 | Xia | |
| 6,543,158 B1 | | 4/2003 | Dieckhaus | |
| 6,549,639 B1 | | 4/2003 | Genest | |
| 6,823,550 B1 | * | 11/2004 | Kantro ..................... 12/142 N |
| 2002/0071597 A1 | * | 6/2002 | Ravitz et al. ............... 382/286 |
| 2002/0122928 A1 | | 9/2002 | Botrie et al. | |
| 2003/0091612 A1 | | 5/2003 | Sabesan | |

* cited by examiner

Primary Examiner—Anthony Stashick
(74) Attorney, Agent, or Firm—Jones Day

(57) ABSTRACT

A method comprises stocking a predetermined number of sets of foot orthotics, each set having a standard arch height that is unique for that set. An arch height of a sole of a foot is measured. Then, an orthotic is selected from the set for which the standard arch height most closely matches the measured arch height.

5 Claims, 5 Drawing Sheets

FOOT ORTHOTIC

TECHNICAL FIELD

The present invention relates to foot orthotics.

BACKGROUND

A foot orthotic is configured to be removably installed in a shoe. Within the shoe, the orthotic lies between an insole of the shoe and a sole of a foot to cushion the foot. An arch of the orthotic supports the arch of the foot.

SUMMARY

A method in accordance with the present invention comprises stocking a predetermined number of sets of foot orthotics, each set having a standard arch height that is unique for that set. An arch height of a sole of a foot is measured. Then, an orthotic is selected from the set for which the standard arch height most closely matches the measured arch height.

Preferably, the predetermined number equals three. The measuring step includes determining the arch height from a footprint of the sole. The orthotics can be heat-softened, and the method further comprises the step, after the selecting step, of pressing the sole against the selected orthotic while the selected orthotic is installed in a shoe in a heat-softened state.

Another method in accordance with the invention comprises engaging a sole of a foot against an imaging device that yields a thermal image of the sole. A characteristic of the sole is determined based on the image.

Preferably, the characteristic is an arch height of the sole. The imaging device includes a thermally sensitive material that exhibits a change in color with a change in temperature. The imaging device is in the form of a plate configured to lie flat on the ground, and the engaging step includes stepping on the device.

A foot orthotic in accordance with the invention is configured to be removably installed in a shoe and comprises an upper layer, a middle layer and a lower layer adhered together. The upper layer is formed of a viscoelastic material. The middle layer is formed of a thermoplastic material. The lower layer is formed of a thermoset material.

Preferably, the thermoplastic material has a softening temperature of about 55–80° C., whereby the orthotic can be pressed by a foot while the middle layer is in a heat-softened state during a custom-molding process but will not heat-soften during normal use

DESCRIPTION

Figure 1:
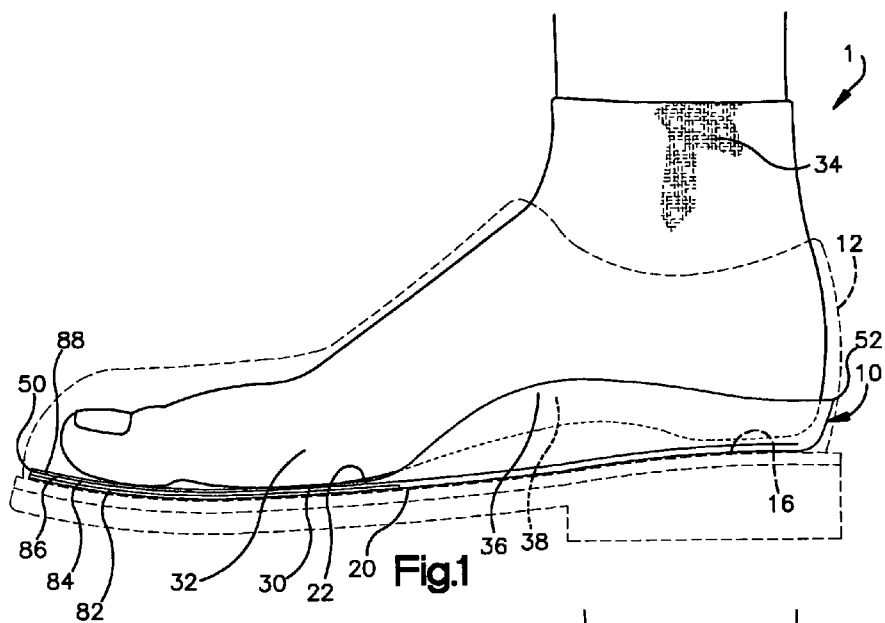
FIG. 1 is a side view of a foot orthotic in accordance with the present invention, shown installed in a shoe and lying between an insole of the shoe and a sole of a foot.

The apparatus 1 shown in FIG. 1 has parts which, as described below, are examples of the elements recited in the claims.

The apparatus 1 includes a foot orthotic 10. The orthotic 10 can be removably installed in a shoe 12, in an installed position in which it lies flat over an insole 16 of the shoe 12. A bottom surface 20 of the orthotic 10 has a shape corresponding to that of the insole 16. A top surface 22 of the orthotic 10 has a shape corresponding to that of a sole 30 of a foot 32, shown covered by a sock 34. The orthotic 10 has elastic and viscoelastic properties to cushion the foot 32. The orthotic 10 also has a medial arch 36 to support a medial arch 38 of the foot 32. The orthotic 10 can be plastically deformed when heated to a heat-softened state. Accordingly, the orthotic 10 can be custom-molded to the shape of the foot sole 30 by a process entailing pressing the foot sole 30 against the orthotic 10 while the orthotic 10 is in the installed position while in the heat-softened state.

Figure 2:
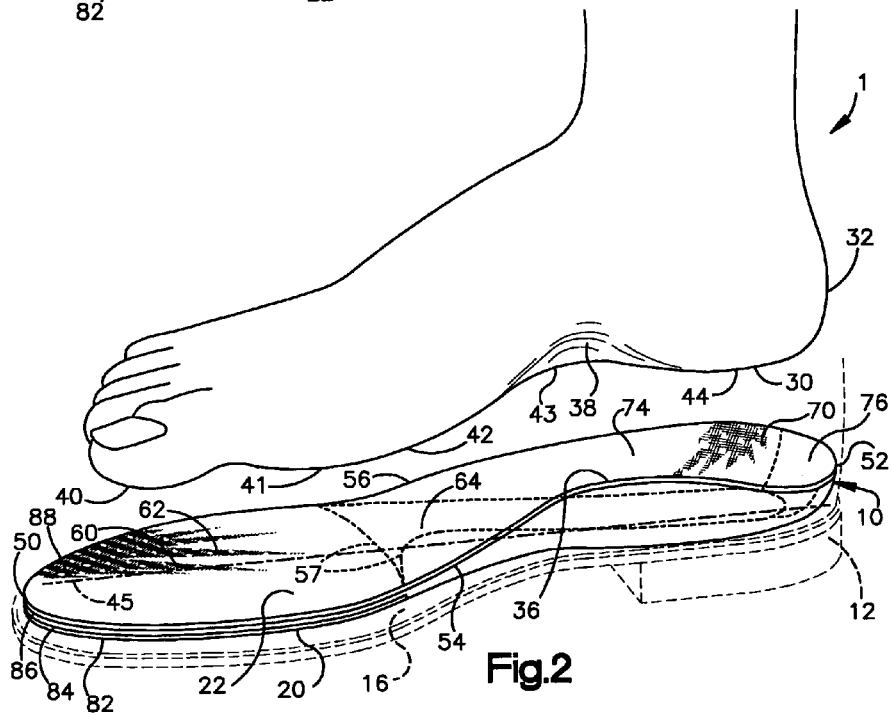
FIG. 2 is a perspective view of the orthotic, the shoe and the foot, showing the foot spaced above the orthotic.

The orthotic 10 is described below with reference to sections of the sole 30 of the foot 32. As shown in FIG. 2, these sections comprise toes 40, metatarsal heads 41, a ball 42, a midfoot 43 and rearfoot 44 (heel). The foot arch 40 is part of the midfoot 43.

The orthotic 10 is elongated along an axis 45, and is bounded axially by front and rear edges 50 and 52. It is bounded transversely by medial (inner) and lateral (outer) side edges 54 and 56.

Figure 3:
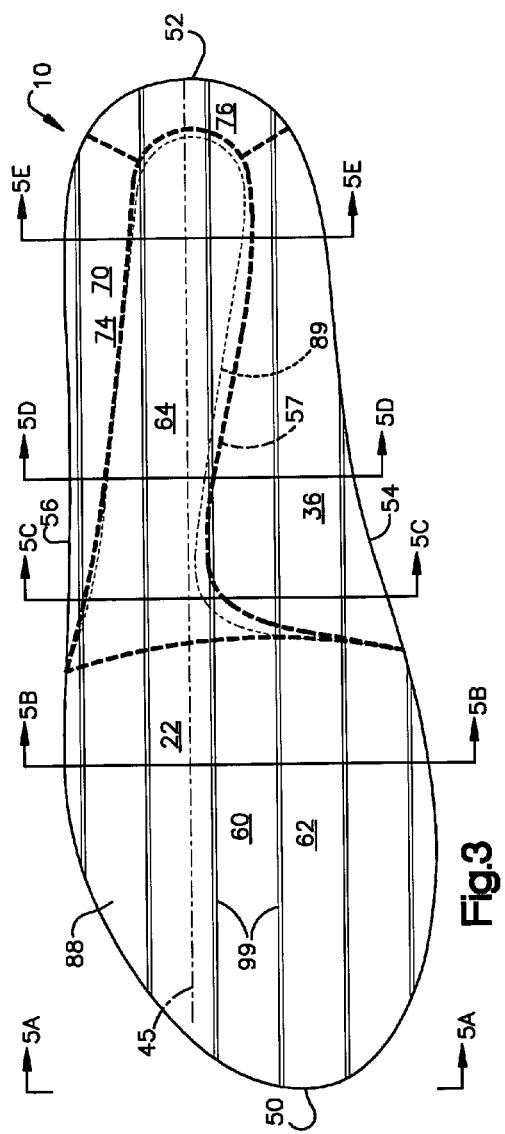
FIG. 3 is a top view of the orthotic.

In FIGS. 2 and 3, sections of the orthotic 10 are delineated by dashed lines 57. The orthotic 10 has a flat section 60 comprising a flat broad front portion 62 and a flat elongated rear portion 64 that projects rearward from the broad front portion 62. The broad front section 62 supports the toes 40, the metatarsal heads 41 and the ball 42 of the foot 32. The elongated rear portion 64 supports the midfoot 43 and the rearfoot 44.

Partially surrounding the narrow rear portion 64 is an upturned section 70. The upturned section 70 comprises the axially-extending medial (inner) arch 36, an axially-extending lateral (outer) arch 74, and an arcuate rear arch 76. The flat narrow rear portion 64 and the surrounding upturned section 70 together cup the midfoot 43 and rearfoot 44.

As shown in FIGS. 4 and 5A–5E, the orthotic 10 is formed as a stack of layers. The layers comprise a lower layer 82, a middle layer 84, an upper layer 86, a top covering 88 that are adhered together. Each layer 82, 84, 86 and 88 has a particular physical property that contributes to the overall characteristics of the orthotic 10.

The lower layer 82 comprises a generally flat piece of material. The material is flexible in that it can bend. It is microcellular in that it has small pores. It is compressible in that it exhibits significant volume change under pressure, due to the pores. It is elastic in that it quickly recovers upon release from applied pressure or torsion. The material can be a thermoset material in that it will not heat-soften at any temperature. Alternatively, the material can a thermoplastic material that will not heat-soften at any temperature applied during the custom-molding process. Accordingly, the material of the lower layer 82 is a material, such as a thermoset, that will not heat-soften below about 90° C. (194° F.) and more preferably not heat soften below about 100° C. (212° F.). This help ensure that the thickness of the lower layer 82 will not vary during the custom-molding process. The material is preferably a polyurethane.

Figure 4:
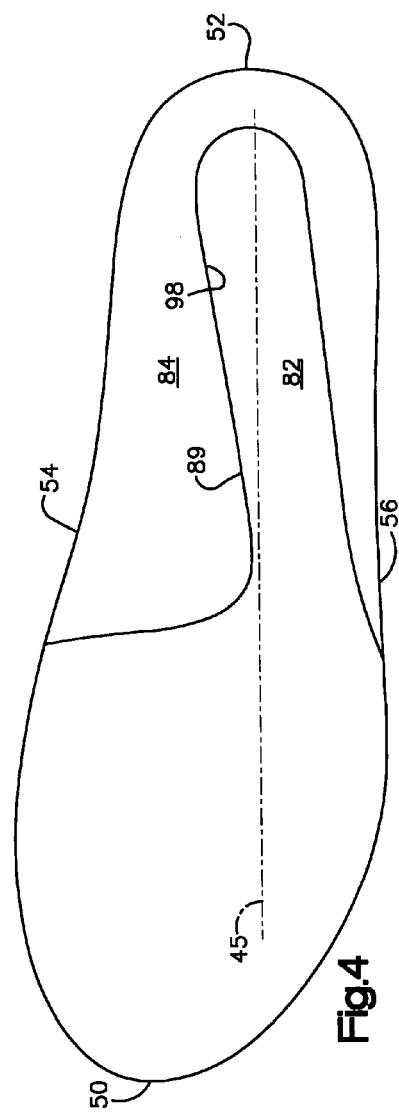
FIG. 4 is a bottom view of the orthotic.
Figure 5A:
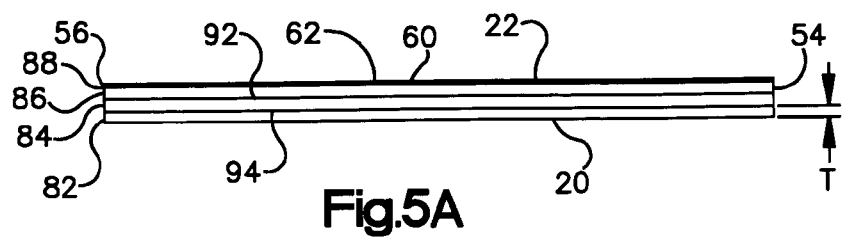
FIGS. 5A–5E are sectional views taken, respectively, at lines 5A–5E of FIG. 3.
Figure 5B:
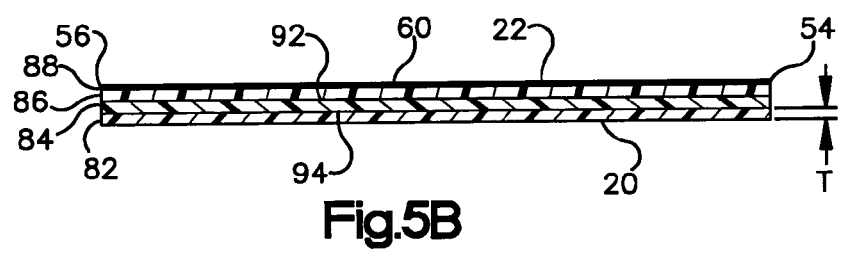
Figure 5C:
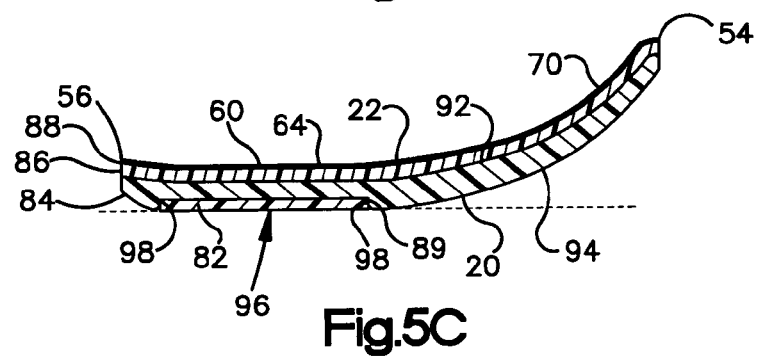
Figure 5D:
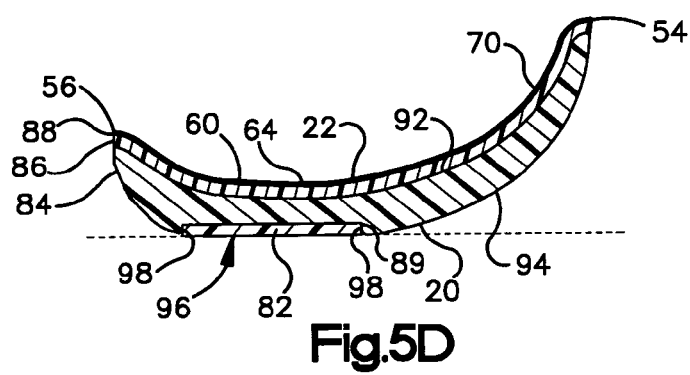
Figure 5E:
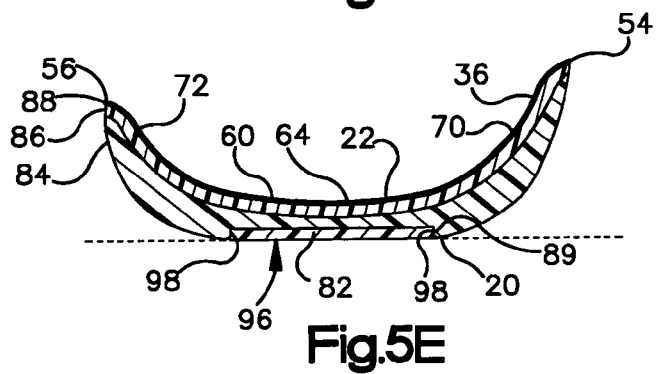

A peripheral edge 89 of the lower layer 82 is denoted by a thin dashed line in the top view of FIG. 3 and by a solid line in the bottom view of FIG. 4. The shape of the lower layer 82 approximately corresponds to the shape of the flat section 60. The lower layer 82 extends across approximately the entire flat section 60 and is absent across approximately the entire turned-up section 70. The lower layer 82 has an approximately uniform thickness T (FIG. 5A) over its entire area bounded by the peripheral edge 89. During the custom-molding process, the lower layer 82 insulates the shoe insole 38 from the high temperature of the middle layer 84, and insulates a section of the middle layer 84 overlying the lower layer 82 from cooling off quickly, and, futher, provides a section of the orthotic 10 that is sure not to thin out.

The middle layer 84 is best shown in FIGS. 4 and 5A–5E. It comprises a material that is microcellular and compressible. This material is flexible and elastic, yet stiffer than the materials of the other layers 82 and 84. The material of the middle layer 84 is a thermoplastic having a softening temperature. Above the softening temperature, the material is in a heat softened state in which it can plastically deform for custom-molding the orthotic 10 to the foot sole 30.

The softening temperature is higher than the highest temperature the orthotic 10 is likely to be exposed to during use, when it is worn in the shoe 12. This prevents plastic deformation of the orthotic 10 during use. Accordingly, the softening temperature is preferably at least about 55° C. (131° F.) and more preferably at least about 60° C. (140° F.). However, the softening temperature must be lower than the temperature applied to the middle layer 84 in the custom-molding process. Accordingly, the softening temperature of the middle layer 84 is preferably up to about 75° C. (167° F.), and more preferably up to about 70° C. (158° F.). The material is preferably an ethylene vinyl acetate (EVA).

The middle layer 84 extends over the entire area of the orthotic 10, bounded by the front, rear, medial and lateral edges 50, 52, 54 and 56. The middle layer 84 is generally flat in the flat section 60 of the orthotic 10 and upturned in the upturned section 70 of the orthotic 10. Most of the stiffness of the orthotic 10, especially in the upturned section 70, is provided by the middle layer 84.

The middle layer 84 has top and bottom surfaces 92 and 94 shown in FIGS. 5A–5E. The top surface 92 is completely covered by the upper layer 86. The bottom surface 94 is covered by the lower layer 82 in the flat section 60 of the orthotic 10 and is exposed in the upturned section 70. The bottom surface 94 of the middle layer 84 defines a recess 96 with sides 98 that closely receive the lower layer 82.

The upper layer 86 overlies the entire middle layer 84. The upper layer 86 comprises a material that is microcellular, compressible and flexible. This material is viscoelastic in that it exhibits slow recovery upon release from applied pressure. During use, this cushions the foot 32 with a soothing viscoelastic material separated from the foot 32 only by the top covering 88. During the custom-molding process, this layer insulates the foot 32 from the temperature of the middle layer 84 and insulates the middle layer 84 from cooling off too quickly. The material is a thermoplastic, with a softening temperature conforming to the ranges stated above for the middle layer 84. Therefore, the material of the upper layer 86 will plastically deform during the custom-molding process but not during use. The softening temperatures of the middle and upper layers 84 and 86 are preferably approximately equal. The material of the upper layer 86 is preferably an ethylene vinyl acetate (EVA).

Alternatively, the material can either be thermoset, or at least not heat soften at temperatures applied during the custom-molding process. This prevents the thickness of the upper layer 86 from varying during the custom-molding process.

The top covering 88 is a fabric overlying the entire upper layer 86. The fabric includes elemental silver. Preferably, the silver is present in the form of silver-containing fibers that are woven into the fabric. The fiber can be a silver-coated nylon fiber, as exemplified by X-Static® fiber sold by Noble Fiber Technologies of Clarks Summit, Pa. As shown in FIG. 3, the silver fibers can be woven into the fabric to form transversely-spaced parallel stripes 99 of silver extending axially along the length of the orthotic 10. The silver-coated fibers can be configured, in terms of amount and location within the fabric, to kill bacteria and fungus, to absorb odor, to conduct heat away from the foot 32 (FIG. 2) to the front and rear edges 50 and 52 of the orthotic 10, to reflect heat emitted by the foot 32 back toward the foot 32 and/or to dissipate static charge.

The top covering 88 is preferably configured, in terms of fiber type and weave, to thermally insulate the foot 32 from the heat of the orthotic 10 during the custom-molding process. This enables the custom-molding temperature, and thus also the softening temperature of the middle layer 84, to be higher than if the top covering 88 were absent. The top layer 88 further provides a surface that is smoother than the upper layer 86, over which the sock-covered foot can slide easily.

Figure 6:
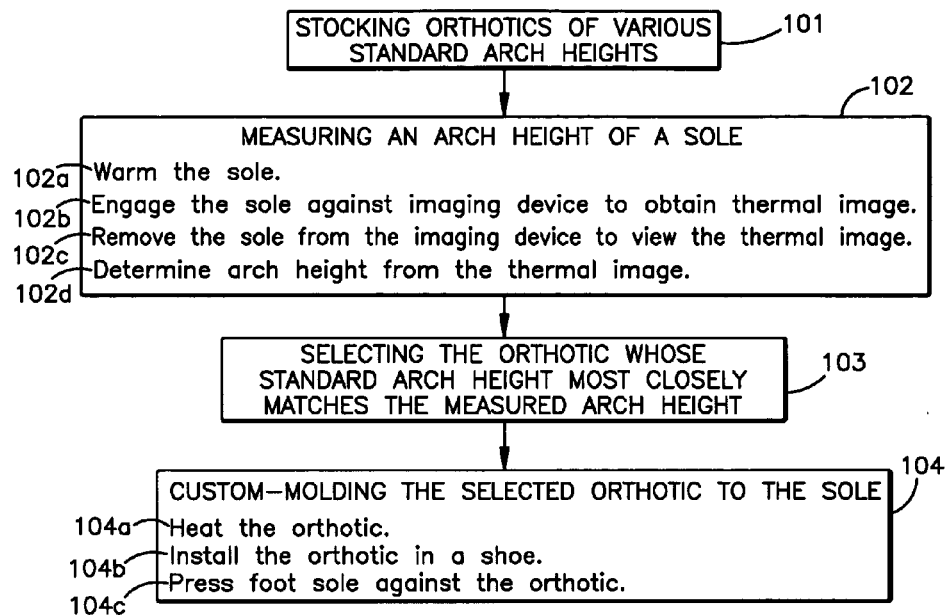
FIG. 6 is a flow chart of steps in a method for use with the orthotic.

The orthotic 10 described above is well suited for use with a method presented in FIG. 6 for providing an orthotic. This method comprises the major steps of stocking 101 orthotics of various standard arch heights, measuring 102 an arch height of a sole, selecting 103 an orthotic whose standard arch height most closely matches the measured arch height, and custom-molding 104 the selected orthotic to the sole. These steps are illustrated by the following example, which takes place in a shoe store.

The stocking step 101 is explained as follows with reference to FIG. 7. The store stocks three sets 121, 122 and 123 of orthotics 126. The orthotics 126 are packaged in boxes 130 hanging on a merchandise rack 132. Each set 121, 122 and 123 comprises orthotics 126 having a standard arch height that is unique for that set. The three standard arch heights for the three sets 121, 122 and 123 in this example are flat, standard and high, respectively, with standard corresponding to a median foot arch height. The middle layers 84 (FIG. 5A) of the orthotics 126 can be color-coded to indicate arch height. For example, the middle layers 84 can be blue, green and yellow, respectively, for orthotics 126 of low arch 121, standard arch 122 and high arch 123.

Both the number of sets and the standard arch height designated for each set are predetermined based on various competing considerations. These considerations include a preference to minimize the number of sets to minimize stocking expenses. There is also a preference to minimize the differences between successive standard arch heights to minimize the extent an orthotic 126 will need to be reshaped in the custom-molding process. There is also a preference that the full range of standard arch heights be sufficiently broad to satisfy the full range of customers' arches likely to be encountered.

In the measuring step 102 (FIG. 6), a customer enters the store to buy orthotics for his feet. The customer's arch height is measured without the customer needing to try on an orthotic. This is done by the customer first removing his shoes and socks from his feet. In a warming sub-step 102a, he warms the soles of the feet by standing on a warming pad 140, shown in FIG. 7, for a short time, such as 30 seconds.

Then, he engages (102*b* in FIG. 6) the soles of his feet against an imaging device 160 that exhibits a change in color with a change in temperature. This is done by simply standing on the imaging device 160 for a short time, such as 15 seconds. The device 160 produces a thermal image of the foot sole, in the form of a thermal footprint, based on the difference in temperature between the sole and the device. Then, the customer removes (102*c* in FIG. 6) his feet from the device to view the thermal image.

The imaging device 160 has the configuration of a flat plate lying on the ground 161. It has no moving parts, no electrical parts and no power cord. It is thus unobtrusive, yet easily accessible by the customer. In this example, it is positioned adjacent to, in front of, the merchandise rack 132. A customer's curiosity about the imaging device 160 will draw him to the merchandise rack 132, and vice versa.

Figure 8:
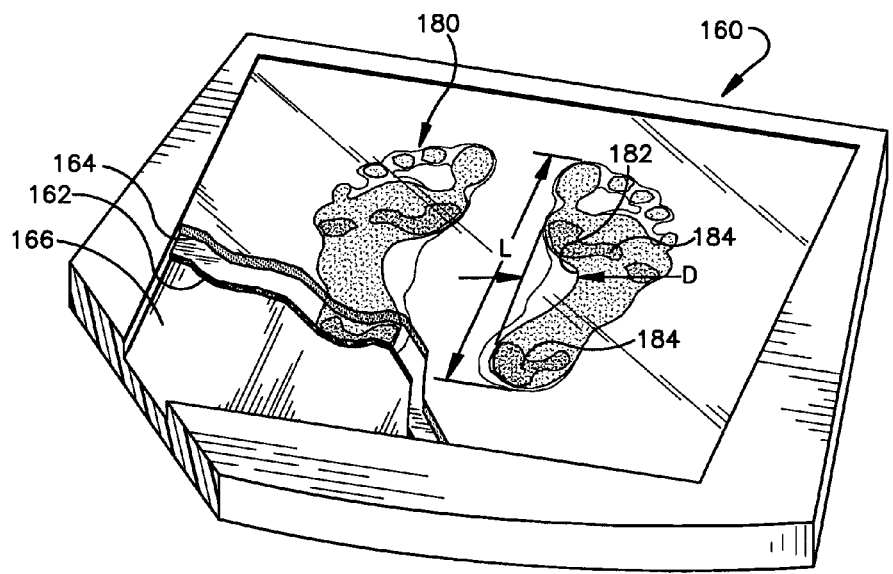
FIG. 8 is a perspective view of a part shown in FIG. 7.

The imaging device 160 is shown in more detail in FIG. 8. It includes a liquid-crystal-based thermal paper 162, which is a thermally sensitive material that exhibits a change in color with a change in temperature. The color change can be a change in shade or intensity of a color, or a change to a different color. The paper 162 is sandwiched between a transparent plastic upper plate 164 to protect the thermal paper from abrasion and a rigid plastic lower plate 166 to prevent the thermal paper 162 from bending. Engagement of the foot sole against the upper plate 164 causes the thermal paper 162 to change color at locations at which the upper plate 164 is close to or contacting the sole. At each location on the thermal paper 162, the color change is more pronounced with closer proximity to the sole and with greater pressure against the sole.

An example 180 of the thermal image produced by the substrate is shown in FIG. 8. The image 180 exhibits a typical inward bow 182 in the arch area. The depth D of the inward bow 182 relative to the length L of the footprint 180 is indicative of the customer's arch type. The image 180 can be used to determine other characteristics of the sole than arch height. For example, pressure points 184, which are locations on the sole that press more strongly against the shoe insole, exhibit more pronounced color change. Conversely, restricted blood flow locations of the sole exhibit less pronounced color change. Any information derived from the thermal image 180 relates to the condition of the sole while bearing down on the ground with full body weight. This is in contrast to the sole being raised off the ground for a visual examination by a physician. The footprint 180 gradually fades and the devise 160 used again.

In a determining sub-step 102*d*, the customer or a store clerk determines the arch height from the thermal image 180, based on the depth D of the inward bow 182. This determination 102*d* can be done objectively, such as by measuring the depth D with a ruler, or subjectively without taking an actual length measurement. The determination sub-step 102*d* can be simply a rough estimate, such as by choosing the most closely matching standard arch height from a choice of the three possibilities (flat, standard and high).

Figure 7:
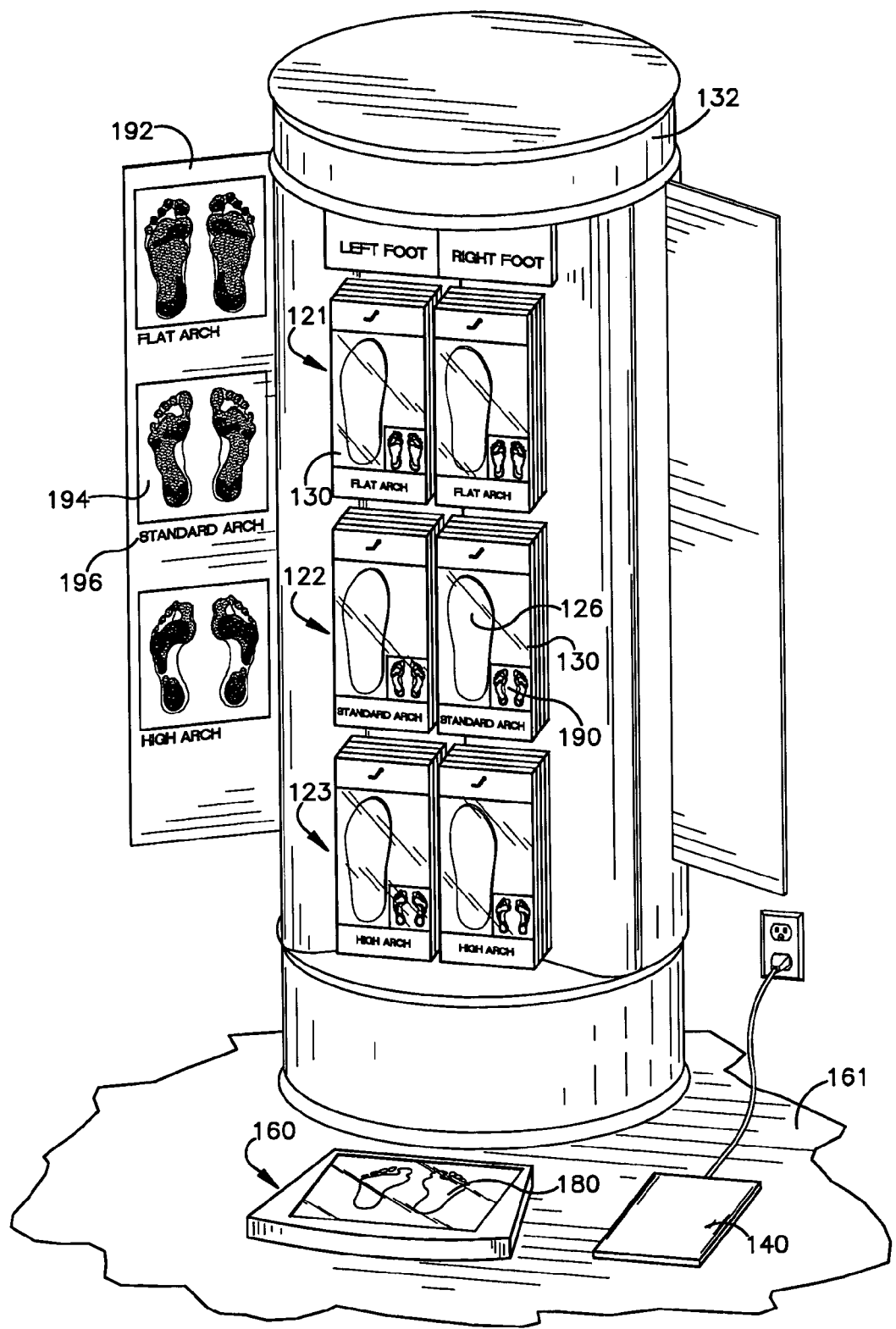
FIG. 7 is a perspective view of an apparatus for use in the method of FIG. 6.

To facilitate the determination sub-step 102*d*, each box 130 in FIG. 7 is imprinted with a reference thermal image 190, or reference footprint, that is indicative of the arch type of the orthotic 126 in the box 130. The customer subjectively compares the thermal image 180 of his own sole with those 190 on the boxes 130, and selects the box 130 providing the closest match. Instead of, or in addition to, the reference images 190 being printed on the boxes 130, reference images 194 can be printed on another medium, such as a poster 192, with each reference image 194 labeled with its corresponding designation 196, such as "flat" or "high" or a numeric measure of arch height.

As described above, the customer removes his socks before stepping on the warming pad 140 and the imaging device 160. The socks are removed so that they do not insulate the feet from the warming pad 140 or the imaging device 160. However, to avoid being barefoot, the customer can place disposable plastic bags over his feet. The wall of the bag should be thin to minimize the insulating effect.

As described above, the customer warms his feet on a warming pad 140 before stepping on the imaging device 160. This is to ensure that the feet are sufficiently warmer than the thermal paper 162 (FIG. 8) to yield a clear thermal image 180. But this pre-warming may not be needed. The need for pre-warming the feet depends on the initial warmth of the feet and a transition-temperature of the thermal paper 162.

As an alternative to the customer's feet being pre-warmed, the thermal paper 162 (FIG. 8) can be pre-warmed to a temperature that is warmer than the feet. Then, when the customer stands on the imaging device 160, different locations on the thermal paper 162 are cooled to different extents, yielding corresponding color changes. The extent of the cooling at each location is related to proximity and pressure of that location with the foot sole. This yields a thermal image that can be used to determine the closest standard arch height.

In the selecting step 103 (FIG. 6), the customer or a store clerk selects an orthotic 126 from the set 121, 122 and 123, shown in FIG. 7, whose standard arch height most closely matches the measured arch height. This can mean simply selecting an orthotic 126 from the set 121, 122 and 123 that is indicated in the measuring step 102. The selected orthotic 10 is installed in the shoe 12 in the installed position shown in FIG. 1. The customer inserts his foot 32 in the shoe 12 to determine whether the fit to his foot 32 is satisfactory. If the fit is unsatisfactory, the fit can be improved by custom-molding the orthotic 10 to the customer's foot in accordance with the following custom-molding step 104 (FIG. 6).

The custom-molding step 104 corresponds to the following process. First, the orthotic 10 is heated (104*a* in FIG. 6) to raise the middle layer 84 to an initial temperature that is above the softening temperature. The initial temperature is sufficiently high such that the middle layer 84 will remain above the softening temperature at least until the end of the custom-molding process. In this example, the orthotic 10 is heated in an oven set at a specified temperature, such as 93° C. (200° F.), for a specified time, such as two minutes. Alternatively, the orthotic 10 can be heated at a specified temperature until a certain portion of the orthotic 10 reaches a specified temperature. This can be done with a thermal tag that changes color at a specified temperature, such as 71° C. (160° F.). The tag is adhered to the bottom or top surface 20 or 22 of the orthotic 10. Then, the orthotic 10 is heated in the oven until the tag changes color.

Next, the orthotic 10 is installed (104*b* in FIG. 6) in the shoe 32 in the installed position shown in FIG. 1. The customer inserts his foot 32, covered by a sock 34, into the shoe 12. He stands upright, for typically 0.5–1 minute, and/or walks around, for typically 2–3 minutes. Doing so presses (104*c* in FIG. 6) the foot sole 30 against the orthotic 10 while the middle layer 84 is still in the heat-softened state and can plastically deform. This is done with sufficient pressure and for sufficient time for the orthotic 10 to conform to the shape of the foot sole 30 from above and the shape of the insole 16 from below. This conformity implies a correspondence in shape without implying an actual match in shape. The conformity can entail bending of the middle layer 84. It can further entail areas of the middle layer 84 that are under greater pressure from the sole 30 being thinned out, with the resulting displaced material moving to areas that are subjected to less pressure. The custom-molding process is thus complete.

During the pressing sub-step 104c, the temperature of the middle layer 84 can be higher than the highest temperature the foot can tolerate, by a certain value. This value is related to the insulating properties of the sock 34, the top covering 88 and the upper layer 86. Based on these considerations, the temperature of the middle layer 84 during the pressing sub-step 104c should not exceed about 80° C. (176° F.).

As indicated above, during the pressing sub-step 104c, the sole is covered and insulated by the customer's own sock. However, the sole can instead be covered by a material with a thickness similar to that of the sock, but with a much higher insulating value than the sock. That would enable the temperature of the middle layer 84 during the pressing sub-step 104c to be correspondingly higher, such as up to 85° C. (185° F.). The softening temperature of the middle layer 84 could then be up to about 80° C. (176° F.). Such an insulating material could be a Styrofoam sheet fashioned into the shape of a sock.

The above explanation of the custom molding process 104 includes considerations relating to the molding and softening temperatures of the middle layer 84. These considerations apply also to the molding and softening temperatures of the upper layer 86 if it, too, has a softening temperature and is configured to plastically deform during the custom-molding process.

As mentioned above, the preferred imaging device 160 (FIG. 8) includes a thermally sensitive material 162 that exhibits a change in color with a change in temperature to yield a thermal footprint 180. Alternatively, the material 162 can be a pressure sensitive material, possibly liquid crystal, that exhibits a change in color with a change in pressure. The resulting footprint 180 would not indicate temperature-related foot characteristics, such as restricted blood flow locations. Also, the customer would not have to remove his socks, because such an alternative imaging device is not based on temperature sensing. The image can fade with time, and the device used again.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have elements that do not differ from the literal language of the claims, or if they include equivalent structural elements with insubstantial differences from the literal language of the claims.

The invention claimed is:

1. A method comprising:
   engaging a sole of a foot against a thermal imaging device to obtain from the device a thermal image of the sole, the imaging device including a thermally sensitive material, that exhibits a change in color with a change in temperature, lying flat over a rigid surface that prevents the material from bending when the sole is engaged against the device; and
   determining a characteristic of the sole based on the thermal image.

2. The method of claim 1 wherein the engaging step includes standing on the imaging device.

3. The method of claim 1 wherein the characteristic is an arch height of the sole.

4. A method comprising:
   warming a thermally sensitive material to a temperature that is warmer than a sole of a foot, the material being part of a thermal imaging device and configured to exhibit a change in color with a change in temperature;
   engaging the sole against the device to obtain from the material a thermal image of the sole based on different locations on the material being cooled by the sole to different extents; and
   determining a characteristic of the sole based on the thermal image.

5. The method of claim 4 wherein the characteristic is an arch height of the sole.

* * * * *